(12) United States Patent
Ito et al.

(10) Patent No.: US 10,074,170 B2
(45) Date of Patent: Sep. 11, 2018

(54) METHOD OF PRODUCING TABLET COMPRISING SPECIFIC EXHAUSTED AIR RELATIVE HUMIDITY

(75) Inventors: Kensuke Ito, Yokohama (JP); Yasuhiro Suzuki, Hiratsuka (JP)

(73) Assignees: FUJI XEROX CO., LTD., Minato-ku, Tokyo (JP); Daiichi Sankyo Company, Limited, Chuo-ku, Tokyo (JP)

( * ) Notice: Subject to any disclaimer, the term of this patent is extended or adjusted under 35 U.S.C. 154(b) by 0 days.

(21) Appl. No.: 14/379,422

(22) PCT Filed: Aug. 23, 2012

(86) PCT No.: PCT/JP2012/071359
§ 371 (c)(1),
(2), (4) Date: Sep. 17, 2014

(87) PCT Pub. No.: WO2013/140639
PCT Pub. Date: Sep. 26, 2013

(65) Prior Publication Data
US 2015/0010758 A1 Jan. 8, 2015

(30) Foreign Application Priority Data
Mar. 19, 2012 (JP) .................. 2012-062605

(51) Int. Cl.
*A61K 9/28* (2006.01)
*A61K 9/30* (2006.01)
(Continued)

(52) U.S. Cl.
CPC ............. *G06T 7/001* (2013.01); *A61J 3/005* (2013.01); *A61K 9/2072* (2013.01);
(Continued)

(58) Field of Classification Search
CPC ......... A23L 35/00; A61K 9/28; A61K 9/2806; A61K 9/20; C09D 101/00
(Continued)

(56) References Cited

U.S. PATENT DOCUMENTS 6,242,496 B1 * 6/2001 Kulkarni ................ A61K 47/12
514/649
7,634,390 B2 * 12/2009 Choi .................. G05B 19/4069
427/2.18
(Continued)

FOREIGN PATENT DOCUMENTS

CN 101663027 A 3/2010
JP 11-178894 A 7/1999
(Continued)

OTHER PUBLICATIONS

Online translation copy of JP 11-178894 (Suzuki et al.), 1999.*
(Continued)

*Primary Examiner* — Hoa T Le
(74) *Attorney, Agent, or Firm* — Sughrue Mion, PLLC

(57) ABSTRACT

A method of producing a tablet in which an uncoated tablet is coated by a coating agent, the method including: a coating process of coating uncoated tablets with a coating agent by spray coating the coating agent onto tablets that are churned and tumbled inside a container, and drying the tablets inside the container by supplying drying air into the container and exhausting air from the container, wherein spray coating conditions, including air supply temperature, air supply rate, and spray speed, are controlled according to the weight of the coating agent with which the uncoated tablets are coated, such that the humidity of air exhausted during spray coating is within a range of from 14% RH to 30% RH.

10 Claims, 16 Drawing Sheets

(51) Int. Cl.
| | |
|---|---|
| *G06T 7/00* | (2017.01) |
| *G01N 21/95* | (2006.01) |
| *A61J 3/00* | (2006.01) |
| *A61K 9/20* | (2006.01) |
| *G06K 9/00* | (2006.01) |
| *G06K 9/62* | (2006.01) |
| *A61J 3/10* | (2006.01) |

(52) U.S. Cl.
CPC ....... *A61K 9/2095* (2013.01); *G01N 21/9508* (2013.01); *G06K 9/00* (2013.01); *G06K 9/00577* (2013.01); *G06K 9/6277* (2013.01); *A61J 3/10* (2013.01); *A61J 2200/40* (2013.01); *A61J 2200/72* (2013.01); *A61K 9/2893* (2013.01); *G06T 2207/30121* (2013.01); *G06T 2207/30204* (2013.01); *Y10T 428/2991* (2015.01)

(58) Field of Classification Search
USPC ............... 427/212, 2.14, 2.18; 424/464, 474
See application file for complete search history.

(56) References Cited

U.S. PATENT DOCUMENTS

| | | | |
|---|---|---|---|
| 2008/0275124 A1* | 11/2008 | Watanabe | A23L 33/175 514/561 |
| 2010/0129446 A1* | 5/2010 | Liu | A61K 9/5073 424/482 |
| 2010/0328687 A1 | 12/2010 | Kimura et al. | |
| 2011/0104277 A1* | 5/2011 | Ma | A61K 9/2813 424/480 |
| 2011/0186629 A1 | 8/2011 | Stuck et al. | |
| 2012/0300985 A1 | 11/2012 | Ito | |
| 2013/0058986 A1 | 3/2013 | Liu et al. | |
| 2015/0086085 A1 | 3/2015 | Ito | |

FOREIGN PATENT DOCUMENTS

| | | |
|---|---|---|
| JP | 2006-31388 A | 2/2006 |
| JP | 2007279812 A | 10/2007 |
| JP | 4103826 B2 | 6/2008 |
| JP | 2010-526110 A | 7/2010 |
| JP | 2011-165095 A | 8/2011 |
| KR | 10-2010-0016306 A | 2/2010 |
| WO | 2008/135090 A1 | 11/2008 |
| WO | 2011099302 A1 | 8/2011 |

OTHER PUBLICATIONS

Brittain et al., Physical characterization of pharmaceutical solids, Pharmaceutical Research, vol. 8, No. 8, 1991.*
Porter et al, Process Optimization Using Design of Experiments, Oct. 1997, Pharmaceutical Technology (Year: 1997).*
Dowwolff Cellulosics, Tablet Coating—A Technical Review—Downloaded online on 2018 (Year: 2018).*
Krutin et al., An Overview: Aqueous film coating technology on Tablets, International Journal of Pahrmaceutical and Chemical Sciences, vol. 1 (3) Jul.-Sep. 2012 (Year: 2012).*
Communication dated Oct. 19, 2015 from the European Patent Office issued in corresponding Application No. 12871766.7.
Communication dated Mar. 8, 2016 from the European Patent Office issued in corresponding Application No. 12871766.7.
Communication dated Jan. 5, 2016 from the Japanese Patent Office issued in corresponding Application No. 2012-062605.
International Search Report of PCT/JP2012/071359, dated Sep. 25, 2012. (PCT/ISA/210).
Communication dated Jan. 17, 2017, from the European Patent Office in counterpart European Application No. 16193012.8.
Chinese Office Action, CN 101663027A, dated Sep. 29, 2016.
Communication dated Sep. 18, 2017 from the Korean Intellectual Property Office in counterpart application No. 10-2016-7033577.
Communication dated Apr. 24, 2016 from the Korean Intellectual Property Office issued in corresponding Application No. 10-2014-7023387.

* cited by examiner

| IDENTIFICATION DATA | REGISTERED IMAGE DATA | PRODUCTION DATA | VERIFICATION HISTORY DATA |
|---|---|---|---|
| 0001 | ...... | ...... | ...... |
| 0002 | ...... | ...... | ...... |
| ...... | ...... | ...... | ...... |
| 10000 | ...... | ...... | ...... |

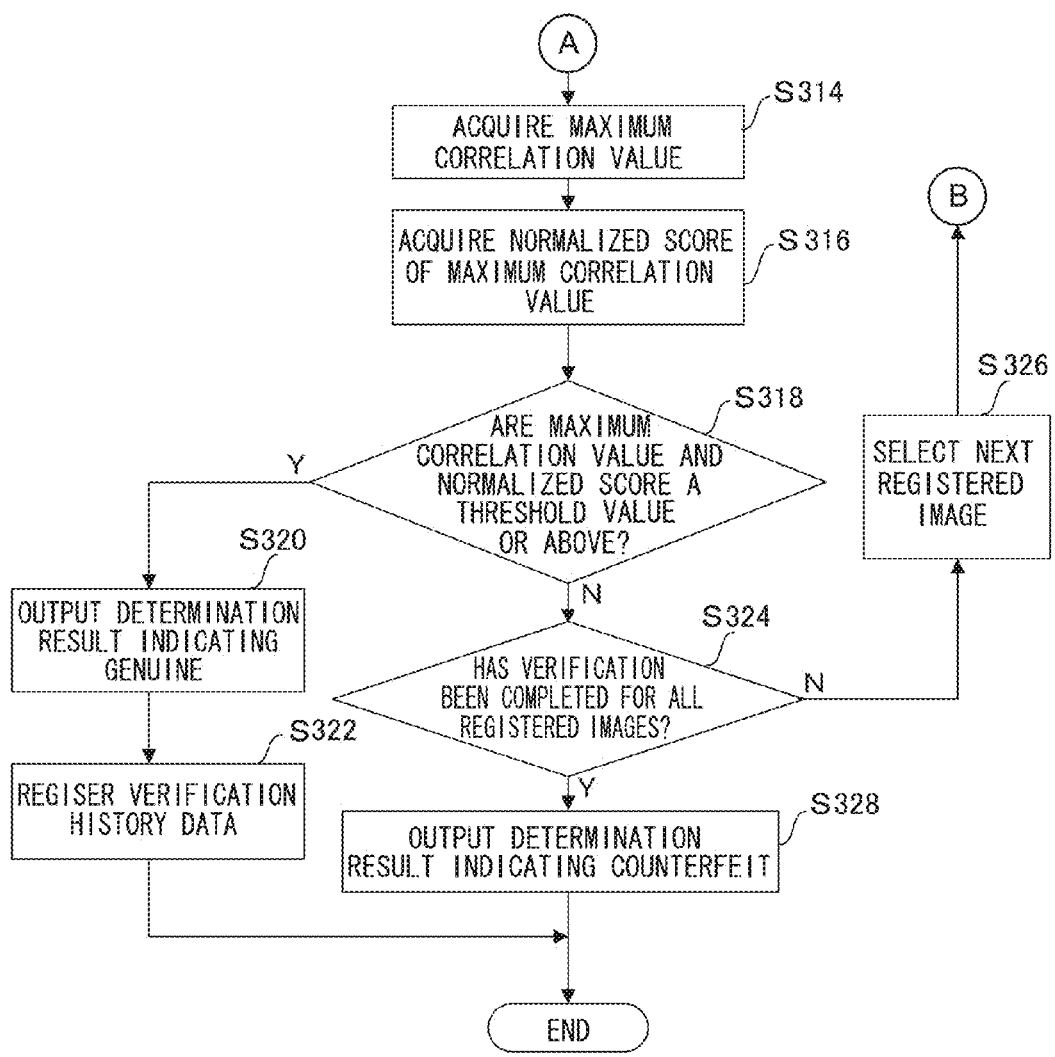

US 10,074,170 B2

METHOD OF PRODUCING TABLET COMPRISING SPECIFIC EXHAUSTED AIR RELATIVE HUMIDITY

CROSS REFERENCE TO RELATED APPLICATIONS

This application is a National Stage Entry of International Application No. PCT/JP2012/071359 filed Aug. 23, 2012, and claims priority based on Japanese Patent Application No. 2012-062605, filed Mar. 19, 2012, the contents of all of which are incorporated herein by reference in their entirety.

TECHNICAL FIELD

The present invention relates to a tablet, a method of producing tablets, a tablet management device, a tablet verification device, and a program storage medium.

BACKGROUND ART

Japanese Patent No. 4103826 describes an authenticity determination method for determining the authenticity of a solid object in which random scannable distinguishing features are distributed along the surface. In this authenticity determination method, reference data expressing features distributed on a genuine solid object are obtained by scanning features of the genuine solid object in advance, and verification data expressing features distributed on a solid object that is subject to determination are derived by scanning features of the solid object subject to determination. Based on the reference data and the verification data, correlation values are computed between data expressing features distributed in a first region of a specific size on one solid object of the genuine solid object or the solid object subject to determination, and data expressing features distributed in a second region of the same size as the first region on the other solid object. This computation is repeated while moving the position of the second region of the other solid object within a region that is larger than the specific size. The authenticity of the solid object subject to determination is determined based on whether or not the maximum value of plural correlation values obtained by this computation is a first specific value or greater, and whether or not a normalized score of the maximum value of the correlation value, obtained by dividing the standard deviation of the correlation values into a value obtained by subtracting an average value of the correlation values from the maximum value of the correlation values, is a second specific value or greater.

SUMMARY OF INVENTION

Technical Problem

An object of the present invention is to provide a method of producing tablets enabling production of tablets that allow unique identification or tracking management of tablets by determining whether or not a tablet is a tablet that is subject to management based on image data of the tablet surface. Another object of the present invention is to provide a tablet produced by the method of producing tablets of the present invention. Yet another object of the present invention is to provide a tablet management device, a tablet verification device and a computer-readable storage medium storing a program that uniquely identifies and performs tracking management of tablets, using tablets produced by the tablet production method of the present invention.

Solution to Problem

In order to achieve the above object, a first aspect of the present invention is a method of producing a tablet in which an uncoated tablet is coated by a coating agent, the method including: a coating process of coating uncoated tablets with a coating agent by spray coating the coating agent onto tablets that are churned and tumbled inside a container, and drying the tablets inside the container by supplying drying air into the container and exhausting air from the container, wherein spray coating conditions, including air supply temperature, air supply rate, and spray speed, are controlled according to a weight of the coating agent with which the uncoated tablets are coated, such that a humidity of air exhausted during spray coating is within a range of from 14% RH to 30% RH.

A second aspect of the present invention is a method of producing a tablet of the first aspect of the present invention, wherein the spray coating conditions are controlled such that in cases in which a proportion of a weight of the coating agent to a weight of the uncoated tablets is 3.6% by weight, a moisture content of the tablets on completion of spray coating is between 1.3% by weight and 2.3% by weight.

A third aspect of the present invention is a method of producing a tablet of either the first aspect or the second aspect of the present invention, wherein the spray coating conditions are controlled such that a temperature of the tablets during spray coating is 47° C. or lower.

A fourth aspect of the present invention is a method of producing a tablet of any one of the first aspect to the third aspect of the present invention, wherein after completion of the coating process, plural tablets are arrayed such that the plural tablets form a line in a predetermined direction; and a marker that identifies an orientation of a predetermined scan region is applied to a surface of each of the arrayed plural tablets, and plural image data is acquired by scanning the predetermined scan region on the surface of each of the arrayed plural tablets.

A fifth aspect of the present invention is a tablet obtained using the method of producing a tablet of any one of the first aspect to the fourth aspect of the present invention, the tablet including a uniquely identifiable random undulating shape on a tablet surface.

A sixth aspect of the present invention is a tablet management device that manages the tablets of the fifth aspect of the present invention, the tablet management device including: an acquisition unit that, for each of plural tablets that are subject to management, scans a predetermined scan region of the tablet surface at a graphic resolution of from 400 pixels per inch to 900 pixels per inch and acquires plural sets of registered image data corresponding to plural registered images; and a storage unit that stores the plural registered image data acquired by the acquisition unit associated with production data of the corresponding tablets.

A seventh aspect of the present invention is the tablet management device of the sixth aspect of the present invention, wherein in cases in which the scan region has a rectangular shape in plan view, a length of a long side of the scan region is set at from 0.9 mm to 2 mm.

An eighth aspect of the present invention is the tablet management device of either the sixth aspect or the seventh aspect of the present invention, wherein the storage unit further stores the plural registered image data associated with verification history data of the corresponding tablets.

A ninth aspect of the present invention is a tablet verification device that performs a verification of a tablet subject to management, using the tablet of the fifth aspect of the present invention as the tablet subject to management, the tablet verification device including: a first acquisition unit that, for each of plural tablets subject to management, acquires plural sets of registered image data corresponding to plural registered images obtained by scanning a first region of a tablet surface at a graphic resolution of from 400 pixels per inch to 900 pixels per inch; a storage unit that stores the plural registered image data acquired by the first acquisition unit; a second acquisition unit that, for a tablet subject to determination, acquires verification image data corresponding to a verification image obtained by scanning a second region of the tablet surface including a region corresponding to the first region at the scan graphic resolution of the registered images; a computation unit that, based on the plural registered image data stored in the storage unit and the verification image data acquired by the second acquisition unit, for each of the plural registered images, extracts from the verification image a partial image that is the size of the first region, compares the extracted partial image against the registered image, and computes a correlation value between the partial image and the registered image; and a determination unit that determines whether or not the tablet subject to determination matches any of the plural tablets subject to management, based on the plural correlation values computed by the computation unit and a predetermined determination criterion.

A tenth aspect of the present invention is the tablet verification device of the ninth aspect of the present invention, wherein during computation, the computation unit repeatedly performs computations while sequentially extracting partial images within the verification image.

An eleventh aspect of the present invention is the tablet verification device of either the ninth aspect or the tenth aspect of the present invention, wherein the determination unit makes determination using at least one determination criterion of: a maximum value of the plural correlation values obtained by the computation unit being a first threshold value or greater; or a normalized score of a maximum value of correlation values, obtained by dividing a standard deviation of the correlation values by a value obtained by subtracting an average value of the correlation values from the maximum value of the correlation values, being a second threshold value or greater A twelfth aspect of the present invention is a program that performs a verification of a tablet subject to management, using the tablet of the fifth aspect of the present invention as the tablet subject to management, the program causing a computer to function as: a first acquisition unit that, for each of plural tablets subject to management, acquires plural sets of registered image data corresponding to plural registered images obtained by scanning a first region of a tablet surface at a graphic resolution of from 400 pixels per inch to 900 pixels per inch; a storage unit that stores the plural registered image data acquired by the first acquisition unit; a second acquisition unit that, for a tablet subject to determination, acquires verification image data corresponding to a verification image obtained by scanning a second region of the tablet surface including a region corresponding to the first region at the scan graphic resolution of the registered images; a computation unit that, based on the plural registered image data stored in the storage unit and the verification image data acquired by the second acquisition unit, for each of the plural registered images, extracts from the verification image a partial image that is the size of the first region, compares the extracted partial image against the registered image, and computes a correlation value between the partial image and the registered image; and a determination unit that determines whether or not the tablet subject to determination matches any of the plural tablets subject to management, based on the plural correlation values computed by the computation unit and a predetermined determination criterion.

Yet another aspect of the present invention is a storage medium stored with the program of the twelfth aspect of the present invention.

Effects of Invention

The first and second aspects of the present invention (method of producing a tablet) enable production of tablets capable of being uniquely identified and tracking managed by making determination as to whether or not a tablet is subject to management based on image data of the tablet surface.

The third aspect of the present invention (method of producing a tablet) enables tablets to be produced without impairing the active ingredients of the tablet.

The fourth aspect of the present invention (method of producing a tablet) enables efficient acquisition of image data of the surface of a tablet subject to management during the tablet production process.

The fifth aspect of the present invention (tablet) enables unique identification and tracking management of tablets by making determination as to whether or not a tablet is subject to management based on image data of the tablet surface.

The sixth aspect of the present invention (tablet management device) enables image data of a tablet surface to be managed associated with production data of the tablet.

The seventh aspect of the present invention (tablet management device) enables acquisition of image data necessary for unique identification of a tablet from the surface of a small tablet.

According to the eighth aspect of the present invention (tablet management device), tracking management of tablets subject to management is made easier than when this configuration is not provided.

The ninth and tenth aspects of the present invention (tablet verification device) enable unique identification or tracking management of tablets by making determination as to whether or not a tablet is subject to management based on image data of the tablet surface.

According to the eleventh aspect of the present invention (tablet verification device), the precision of unique identification of a tablet is raised compared to when this configuration is not provided.

The twelfth aspect of the present invention (program) enables unique identification or tracking management of tablets by making determination as to whether or not a tablet is subject to management based on image data of the tablet surface.

BRIEF DESCRIPTION OF DRAWINGS

FIGS. 10A and 10B illustrate a flow chart illustrating a processing routine of "tablet verification processing".

DESCRIPTION OF EMBODIMENTS

Detailed explanation follows regarding an example of an exemplary embodiment of the present invention, with reference to the drawings.

Tablet and Undulating Shape of Tablet Surface

Explanation follows regarding a tablet and an undulating shape of the tablet surface.

A tablet according to the present exemplary embodiment is a tablet with a random undulating shaped surface. Tablets with random undulating shaped surfaces are tablets having undulating shapes uniquely identifiable using an identification method similar to the verification method of paper fingerprints described in Japanese Patent No. 4103826. More specifically, the undulating shape of a predetermined scan region on the tablet surface is scanned at a predetermined graphic resolution, and the tablets are uniquely identifiable based on the acquired image data.

Subjecting the tablets having random undulating shapes on their surfaces to management enables the unique identification and tracking management of hundreds of millions, or trillions, of tablets through the distribution process by pre-registering image data of the surface of the tablets that are subject to management, and determining whether or not a tablet is subject to management based on the registered image data. Explanation regarding a method for uniquely identifying tablets is given later.

Tablets, such as medicinal and dietary tablets, include uncoated tablets in which active ingredients with additives, such as excipients, are made into a tablet form, and coated tablets that are formed by uncoated tablets coated with a coating agent. Coated tablets include sugar coated tablets and film coated tablets in which uncoated tablets are covered with a water soluble polymer. Generally sugar coated tablets have a flat surface without a random undulating shape. Uncoated tablets have an undulating shaped surface in accordance with the granules making up the tablet, and do not always have random undulating shapes.

In the present exemplary embodiment, using film coated tablets, a random undulating shape is intentionally imparted to the tablet surface by coating. The surfaces of tablets subject to management are always formed with random undulating shapes. The method of producing tablets described below enables forming the random undulating shape on the surface of produced tablets, so as to enable unique identification of tablets based on image data. In the following explanation, film coated tablets are referred to as "tablets" if it is not necessary to distinguish them from uncoated tablets or sugar coated tablets.

Figure 1A:
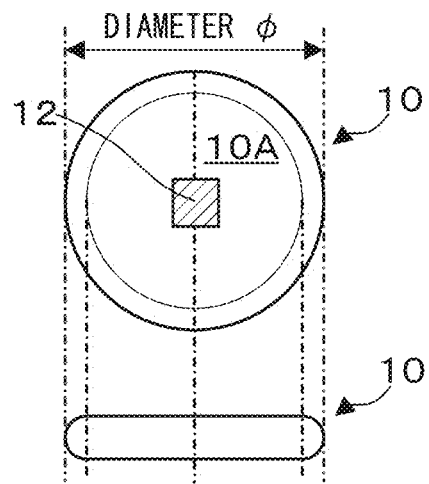
FIG. 1A is a plan view and a cross-sectional view illustrating an example of the external shape of a tablet.

FIG. 1A, FIG. 1B, FIG. 1C, and FIG. 1D each include a plan view and a cross-sectional view illustrating the external shape of a tablet. As illustrated in FIG. 1A, a tablet 10 normally has a circular or oval shape in plan view. For tablets with a circular shape in plan view, the diameter φ of the tablet 10 is approximately 6 mm to approximately 9 mm. For tablets with an oval shape in plan view, the long diameter φ of the oval is approximately 8 mm to approximately 18 mm. The corners of the external perimeter portion of the tablet 10 are beveled for the purpose of facilitating swallowing, and the like. As viewed from the side, a surface 10A of the tablet 10 is accordingly not flat across the entire face, and the external perimeter portion is formed with a circular arc with a predetermined radius of curvature R (R).

Figure 1B:
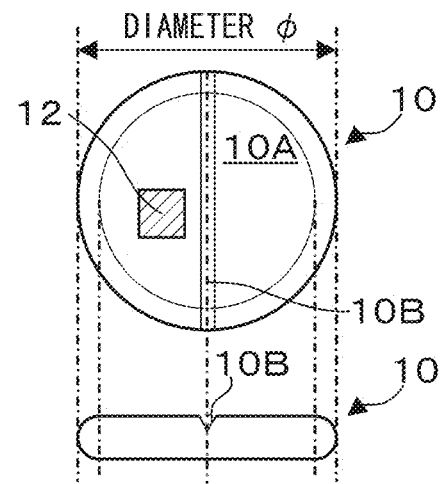
FIG. 1B is a plan view and a cross-section illustrating another example of the external shape of a tablet.
Figure 1C:
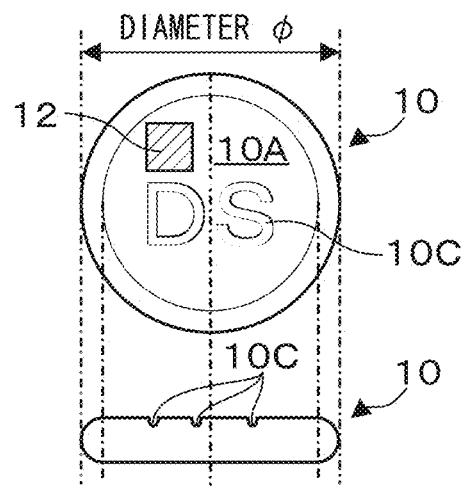
FIG. 1C is a plan view and a cross-sectional view illustrating another example of the external shape of a tablet.
Figure 1D:
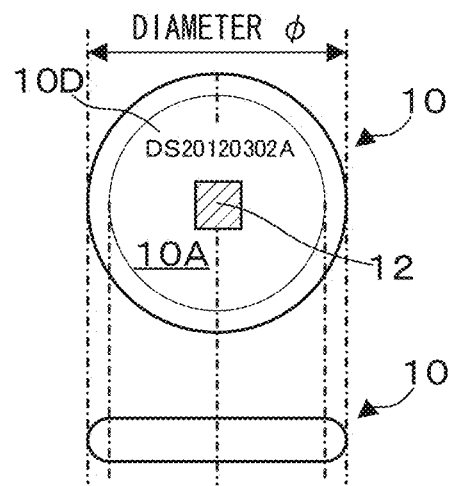
FIG. 1D is a plan view and a cross-sectional view illustrating another example of the external shape of a tablet.

The tablet 10 may include a break line 10B for breaking the tablet, as illustrated in FIG. 1B. The tablet 10 may include an imprint 10C representing an identification symbol (letter or number) for identifying the tablet, as illustrated in FIG. 1C. The surface 10A of the tablet 10 may include print 10D representing an identification symbol, as illustrated in FIG. 1D. As described below, the break line 10B, the imprint 10C, and the print 10D described above are utilized as markers for identifying the position and orientation of the scan region of a registered image when a verification image is acquired.

Figure 2:
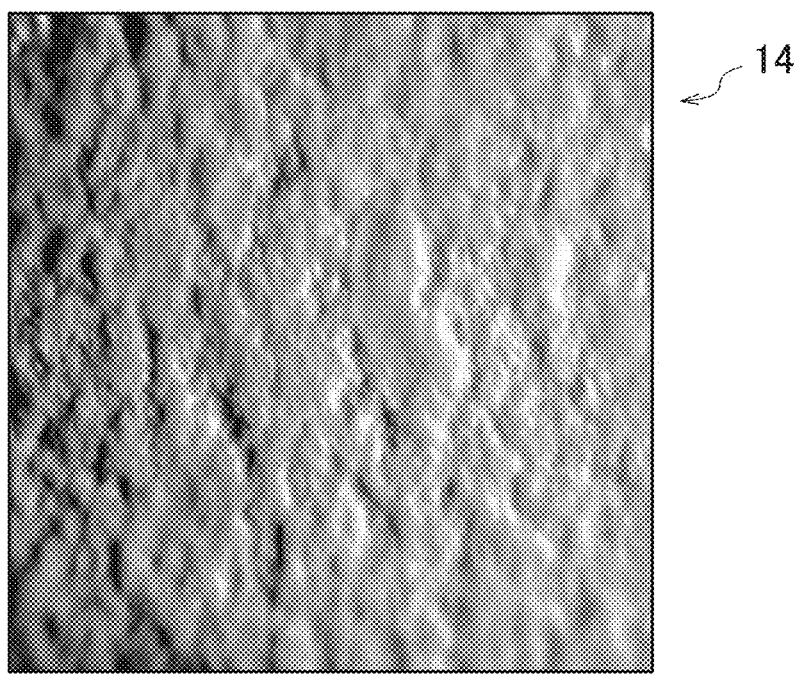
FIG. 2 is an enlarged photograph imaging the surface of a tablet.

FIG. 2 is an enlarged photograph imaging the surface of a tablet. As is apparent from FIG. 2, the tablet 10 according to the present exemplary embodiment has a surface 10A with a random undulating shape. As illustrated in each of FIG. 1A, FIG. 1B, FIG. 1C, and FIG. 1D, a scan region 12 of the tablet 10 is imaged by a close-up camera, image sensor, or the like, and an image (registered image) is acquired of the scanned undulating shape of the tablet surface 10A. In practice, a range wider than the scan region 12 is imaged, and an image of the scan region 12 is extracted from the captured image as the "registered image".

Image data of the acquired image is stored as "registered image data". The scan region 12 is selected from a flat region of the tablet surface 10A in order to obtain sufficient depth of field in the close-up imaging. The scan region 12 is also set on the surface 10A so as to avoid the break line 10B, the imprint 10C, and/or the print 10D if the tablet 10 includes the break line 10B or the like as described above.

The scanning graphic resolution of the tablet surface 10A, namely the graphic resolution of the registered image formed by imaging the scan region 12 of the surface 10A, is in a range of from 400 pixels per inch to 900 pixels per inch. Technology is described in the Japanese Patent No. 4103826 for scanning a random undulating shape of fibers formed on the surface of paper, as "paper fingerprints". Comparing tablets with paper, the robustness of tablets to mechanical impact and friction is not as high as that of paper. Image data is impaired if defects and scratches occur on the surface of tablets. For this reason, if the graphic resolution is too high, while the graphic resolution is increased, stable acquisition of image data becomes difficult.

If the graphic resolution is too low, image data is stably acquired, but there is an increase in the surface area of the scan region 12 in order to obtain the volume of data required to uniquely identify the tablets. However, the diameter φ of the tablet 10 that is circular shaped in plan view is normally approximately 6 mm to approximately 9 mm. Moreover, the break line 10B or the like is preferably avoided. There is accordingly a limitation to increasing the surface area of the scan region 12 of the tablet 10. In other words, it is possible to set the scan region 12 on the surface 10A of a small tablet 10 by limiting the size of the scan region 12.

Consequently, by setting the graphic resolution of the registered image within the range of from 400 pixels per inch to 900 pixels per inch, the image data required for uniquely identifying the tablets can be stably obtained from tablets with a small diameter φ. If the graphic resolution of the registered image is 600 pixels per inch or fewer, then the image data required for uniquely identifying the tablets is even more stably acquired.

There are no particular limitations to the shape of the scan region 12, and, for example, a rectangular shape, such as a square shape, in plan view may be selected. In the present exemplary embodiment, explanation follows regarding a case in which the shape of the scan region 12 is a square shape. The length of one side of the square shaped scan region 12 in plan view is in a range of from 0.9 mm to 2 mm, according to the graphic resolution of the registered image described above, or the diameter φ (or the long axis φ) of the tablet 10. For example, the scan region 12 may be set with a size of "1.4 mm×1.4 mm (32 pixels×32 pixels)" when the registered image has a graphic resolution of 600 pixels per inch.

Note that a scan region 32 of a tablet 30 that is subject to determination, described later, is set at the size of the scan region 12 of the tablet 10 or greater. If the tablet 30 is the same tablet as the tablet 10, the scan region 12 is included in the scan region 32, and a registered image 14 is included in a verification image 34. The length of one side of the square shaped scan region 32 in plan view is in a range of from 2 mm to 4 mm. For example, the scan region 32 may be set with a size of "2.8 mm×2.8 mm (64 pixels×64 pixels)" when the verification image has a graphic resolution of 600 pixels per inch.

Method of Producing Tablets

Explanation follows regarding a method of producing tablets.

A production process of a film coated tablet generally includes a tablet forming process, a coating process, a printing process, a selection process, and a filling and packaging process. These processes are performed in the above sequence. The printing process may be omitted. In the tablet forming process, uncoated tablets are produced by mixing the active ingredients with additives such as excipients, and compression molding the mixture to form tablets. A break line and/or imprint may be formed in the uncoated tablets in the tablet forming process. In the coating process, the surface of the uncoated tablets is coated with a coating agent by spray coating, thus producing the film coated tablets.

In the printing process, with the tablets in an arrayed state, an identification symbol or the like is printed on the tablet surface using offset printing or the like. In the selection process, with the tablets in an arrayed state, the tablets are imaged one tablet at a time, and selected. Normally, plural cameras are arranged to perform imaging from plural directions. The captured images are checked, and any tablets found to have defects, such as adhered foreign objects or cracks, are discarded at the selection process. During the filling and packaging process, normal tablets are filled into a container, or packed in individual packaging.

In the present exemplary embodiment, the spray coating conditions are controlled during the coating process so as to intentionally form a random undulating shape on the tablet surface. Normally, spray coating conditions of coated tablets are controlled to raise surface smoothness of the tablets, from the perspectives of the quality of external appearance and ease of printing. In the method of producing tablets according to the present exemplary embodiment, random undulating shapes are formed on the surface of the tablets so as to enable unique identification of the tablets based on image data. The method of controlling the spray coating conditions therefore also differs from conventional methods of controlling spray coating conditions.

When spray coating the tablets, the tablets are churned and tumbled inside a container, and the coating agent is sprayed onto the churned and tumbled tablets inside the container. The tablets are dried in the container by supplying drying air into the container and exhausting air from the container. The spray coating onto the tablets is performed using a commercially available coating device such as a pan coating machine. Examples of pan coating machines include the "Driacoater", manufactured by Powrex Corporation, and the "Hicoater", manufactured by Freund Corporation. Rotating drum-type containers in pan coating machines are referred to as "(coating) pans".

The coating process with spray coating includes a loading process, a temperature raising process, a spray coating process, a drying process, and a cooling process. These processes are performed in the above sequence. In the loading process, the uncoated tablets are loaded inside the container of the coating device. In the temperature raising process, the uncoated tablets inside the container are warmed. In the spray coating process, the coating agent is spray coated onto the uncoated tablets. In the drying process, the tablets are dried after completion of the spray coating process.

Control parameters of the coating device include, for example, air supply temperature, air supply rate, spray liquid speed (sprayed liquid speed), spray air amount (sprayed air amount), and pan revolution speed. These parameters are controlled when spray coating the tablets in order to manage the tablet temperature and tablet moisture content value during the spray coating. The inventors found after careful investigation that unique identification of tablets based on image data is enabled when the tablet moisture content value on completion of the spray coating process is a higher than normal value. Specific experimental results are explained in the Examples.

However, the tablet moisture content value at the time of completion of the spray coating process varies according to the "film amount", this being the weight of the coating agent with which the uncoated tablets are covered. Further investigation was accordingly carried out, focusing on the "humidity of exhausted air" as a parameter expressing the drying efficiency of the overall system, on the hypothesis that the undulating shape of the coated tablet surface is determined by the drying efficiency of the overall system. The "humidity of exhausted air" is a parameter that is not affected by the film amount. The lower the humidity of the exhausted air, the higher the drying efficiency, and the greater the decrease in the tablet moisture content value.

Figure 3:
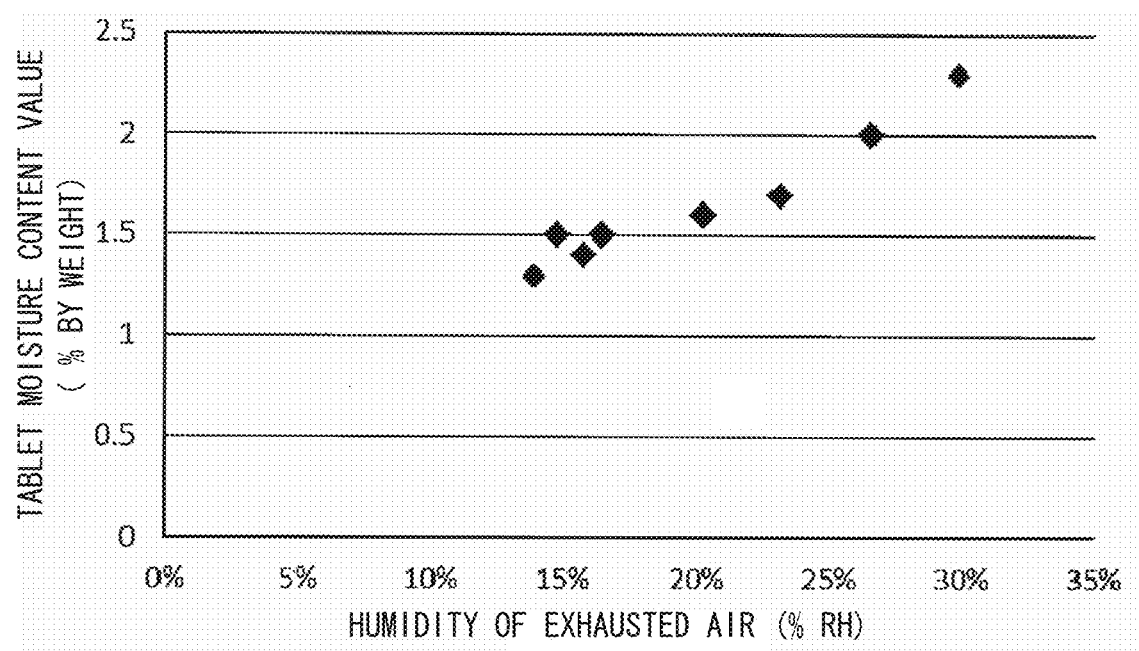
FIG. 3 is a graph illustrating a relationship between the humidity of exhausted air and tablet moisture content value.

FIG. 3 is a graph illustrating a relationship between the humidity of exhausted air and the tablet moisture content value. The horizontal axis indicates the humidity of exhausted air described above, and the vertical axis indicates the tablet moisture content value. The "humidity of exhausted air" is a ratio of the amount of water vapor in the exhausted air (water vapor partial pressure) against a saturated water vapor amount at the same temperature as the exhausted air (saturated water vapor partial pressure). The "humidity of exhausted air" therefore refers to relative humidity, and uses the unit "% RH". The "tablet moisture content value" is the moisture content ratio at the time of completion of the spray coating process, measured at a heating temperature of 80° C. using heated moisture-loss method determination, and uses the unit "% by weight".

As illustrated in FIG. 3, it can be seen that the tablet moisture content value at completion of the spray coating process increases proportionally to the humidity of exhausted air when the relationship between the humidity of exhausted air and the tablet moisture content value is plotted over a range enabling unique identification of tablets based on image data.

This result demonstrates that in the spray coating process of the coating process, random undulating shapes are formed on the tablet surface to a degree enabling unique identification of tablets based on image data by setting the humidity of exhausted air at between 14% RH and 30% RH. In other words, a target tablet moisture content value at completion of the spray coating process can be achieved through the simple method of controlling the "humidity of exhausted air" in the spray coating process, thereby enabling the formation of random undulating shapes on the tablet surface.

A tablet produced with the humidity of exhausted air at 14% RH corresponds to a tablet according to Example 1, described later. The tablet according to Example 1 is at a boundary enabling unique identification of tablets. When the humidity of the exhausted air is below 14% RH, the randomness of the undulating shapes formed on the tablet surface decreases (becomes smoother), making unique identification of tablets based on image data difficult.

A tablet manufactured with the humidity of exhausted air at 30% RH corresponds to a tablet according to Example 2, described later. The tablet according to Example 2 is well-suited to the unique identification of tablets. However, when the humidity of exhausted air exceeds 30% RH, the tablet moisture content value becomes too high, leading to tablet defects such as imprinting being filled by the coating agent. It is conjectured that such defects occur due to the thickness of the film becoming uneven or the film lifting off, for example, due to the tablet moisture content.

Note that the materials used for the uncoated tablets and the coating agent may be conventional, known materials. Namely, the method of producing tablets described above enables tablets to be obtained formed with surfaces with random undulating shapes to a degree enabling unique identification of the tablets based on image data even if the materials used for the uncoated tablets and the coating agent are conventional, known materials.

In addition to active ingredients (main components), excipients, disintegrants, and binders, the uncoated tablets may also include additives such as fluidizers, lubricants, colorants, sweeteners, and flavorings. Moreover, in addition to a water soluble polymer film base, the coating agent may also include additives such as plasticizers, lubricants, light blocking agents, and pigments. The additives are dissolved or dispersed in the aqueous solution film base of the coating liquid. The concentration of the coating agent is normally from 1% by weight to 30% by weight.

The film base may be selected as appropriate from, for example, a gastrosoluble film base, or an enteric or slow-release film base, as suited to the purpose of the tablet. Examples of gastrosoluble film bases include: cellulose derivatives such as hydroxypropyl cellulose, or hydroxypropylmethyl cellulose; synthetic polymers such as polyvinyl acetal diethylamino acetate, aminoalkyl methacrylate copolymer, or polyvinyl pyrrolidone; and dextrin, pullulan, zein, sodium alginate, gelatin, and saccharides.

Examples of plasticizers include, for example, macrogol (polyethylene glycol), triethyl citrate, triacetin, medium chain triglycerides, and glycerin. Examples of lubricants include talc, stearic acid, magnesium stearate, sucrose esters of fatty acids, and hydrogenated oil. Examples of light blocking agents or pigments include metal oxides such as titanium oxide, yellow ferric oxide, red ferric oxide, or black ferric oxide, and tar based pigments.

Moreover, in the present exemplary embodiment, a camera or image sensor that images the scan regions 12 of the tablets 10 may be disposed facing the tablets that are in an arrayed state during the printing process or the selection process, and registered images may be acquired for each of the tablets 10 (see FIG. 1A, 1B, 1C, 1D and FIG. 2). For example, plural of the tablets 10 in an arrayed state in the printing process may each be printed with an identification symbol or the like at the same position on the surface 10A. In such cases, the scan region 12 may be set using the identification symbols or the like printed on the surface 10A as a reference. The scan region 12 of each of the plural arrayed tablets 10 may be imaged to acquire registered images of each of the tablets 10. The printed identification symbols or the like are used as markers for identifying the position and orientation of the scan region of a registered image when a verification image is acquired.

Tablet Management System
Overall System Configuration

Explanation follows regarding a tablet management system.

Figure 4:
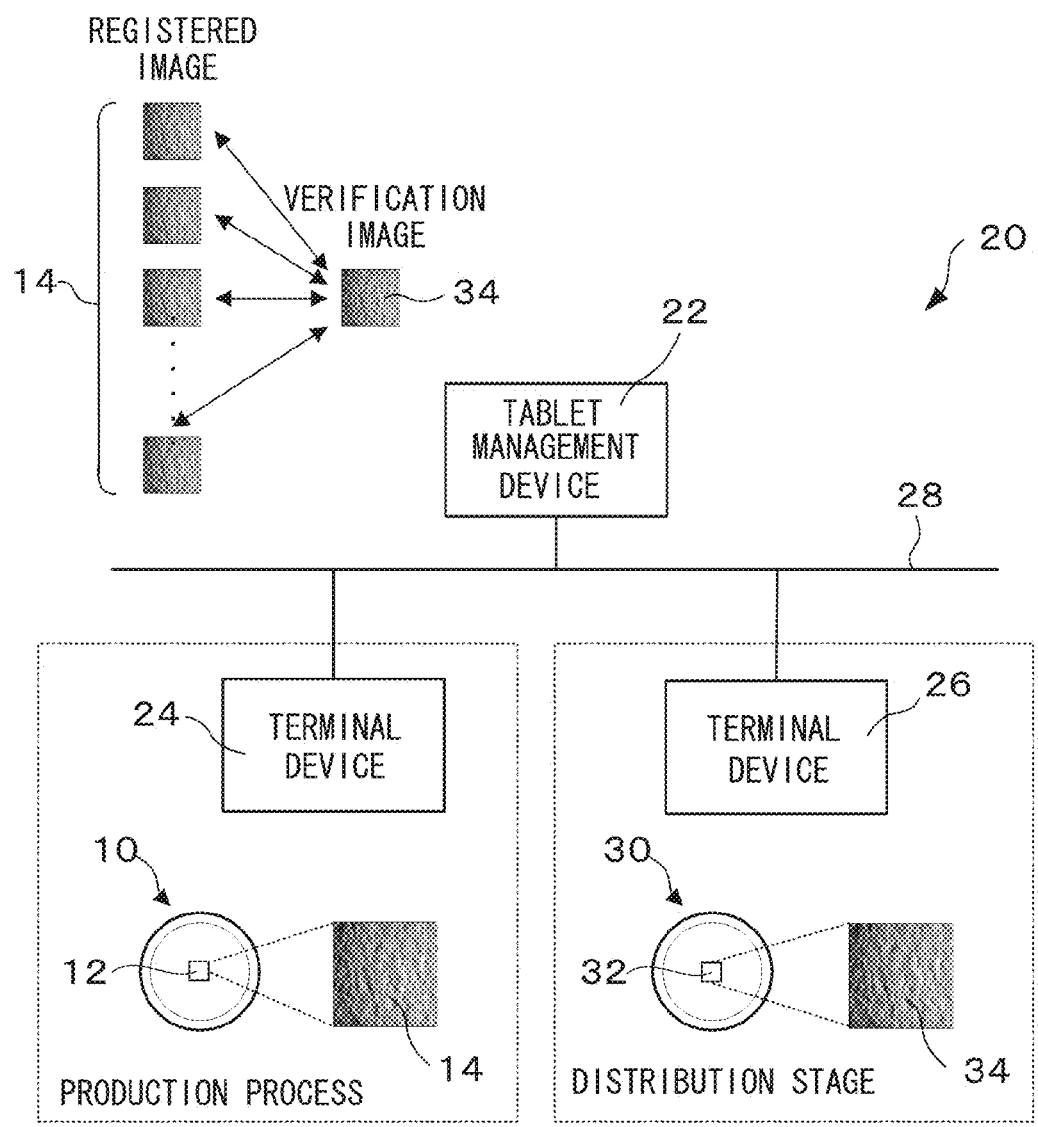
FIG. 4 is a schematic drawing illustrating an example of an overall configuration of a tablet management system.

FIG. 4 is a schematic drawing illustrating an example of an overall configuration of a tablet management system. As illustrated in FIG. 4, a tablet management system 20 includes a tablet management device 22 that is a database, a terminal device 24 that is deployed in a production process, and a terminal device 26 that is deployed in a distribution stage. The tablet management device 22, the terminal device 24, and the terminal device 26 are connected together through a wired or wireless communications line 28. The tablet management device 22, the terminal device 24, and the terminal device 26 are respectively configured by data processing devices and peripheral devices of a computer or the like used by a user.

For example, the terminal device 24 deployed in the production process images the scan regions 12 of plural tablets 10 that are subject to management, and acquires image data corresponding to registered images 14. The terminal device 24 instructs the tablet management device 22 to register the registered images 14. The tablet management device 22 stores the image data of the registered images 14 acquired from the terminal device 24, associated with production data of the tablet 10 corresponding to the registered image 14. The registered image 14, and the production data of the tablet 10 corresponding to the registered image 14, are thereby registered in a database for the plural tablets 10 subject to management.

The terminal device 26 deployed in the distribution stage images the scan region 32 of the tablet 30 that is subject to determination, and acquires image data corresponding to the verification image 34. The terminal device 26 instructs the tablet management device 22 to verify the verification image 34 with the registered images 14. The tablet management device 22 verifies the verification image 34 acquired from the terminal device 26 against each of the plural registered images 14 registered in the database, and searches for a registered image 14 that matches the verification image 34.

In cases in which a registered image 14 matching the verification image 34 is found, the tablet 30 is uniquely identified as being the same tablet as the tablet 10 corresponding to the registered image 14. Namely, the tablet 30 is determined to be a "genuine" tablet that is subject to management. The verification result (determination result) is transmitted to the terminal device 26, and the user of the terminal device 26 is notified.

Production data of the tablet 10 corresponding to the registered image 14 is also acquired. Moreover, if the tablet management device 22 has found a registered image 14 matching the verification image 34, then verification history data for the registered image 14 is stored associated with the tablet 10. Tracking management of the tablet 10 is performed by storing the verification history data associated with the tablet 10.

Note that this configuration of the tablet management system is merely an example thereof, and there is no limitation thereto. For example, the terminal device 24 may be omitted, and the tablet management device 22 may be deployed in the production process. In such cases, an imaging section 38 of the tablet management device 22 images the scan regions 12 of plural tablets 10 that are subject to management, and acquires image data corresponding to the registered images 14 (see FIG. 5).

Tablet Management Device

Explanation follows regarding an electrical configuration of a tablet management device.

Figure 5:
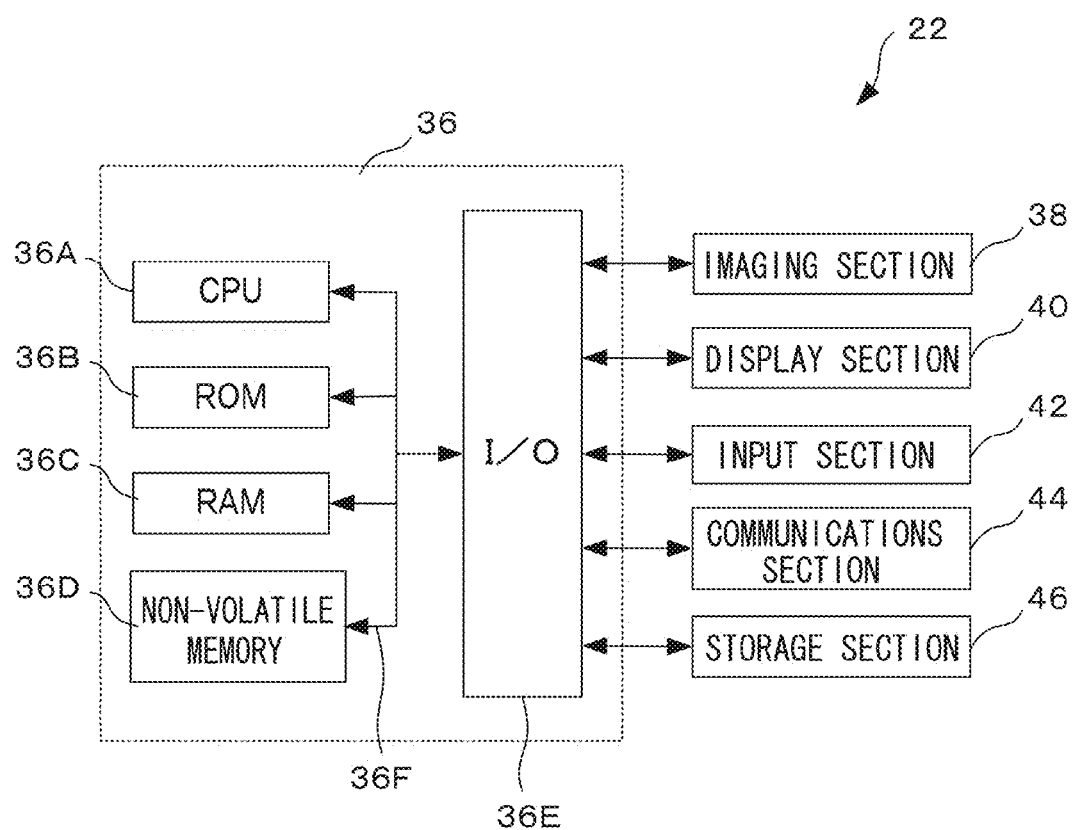
FIG. 5 is a block diagram illustrating an example of an electrical configuration of a tablet management device.

FIG. 5 is a block diagram illustrating an example of an electrical configuration of a tablet management device. As illustrated in FIG. 5, the tablet management device 22 is configured by data processing devices such as computers and peripheral devices, and includes a data processing device 36, the imaging section 38 such as a camera or image sensor, a display section 40 such as a display, an input section 42 such as a mouse and/or keyboard, a communications section 44 that functions as an interface for communicating with external devices, and a storage section 46 such as a hard disk.

The data processing device 36 includes a Central Processing Unit (CPU) 36A, Read Only Memory (ROM) 36B stored with various programs, Random Access Memory (RAM) 36C used as a work area while programs are being executed, non-volatile memory 36D in which various data is stored, and an input/output interface (I/O) 36E. The CPU 36A, the ROM 36B, the RAM 36C, the non-volatile memory 36D, and the I/O 36E are each connected together through a bus 36F.

The imaging section 38, the display section 40, the input section 42, the communications section 44, and the storage section 46 are each connected to an I/O 20E of the data processing device 36. The data processing device 36 controls each of the imaging section 38, the display section 40, the input section 42, the communications section 44, and the storage section 46, and performs various computations.

In the present exemplary embodiment, a control program for executing "tablet management processing", described later, is pre-stored in the storage section 46. The control program is read from the storage section 46 and executed by the CPU 36A. Note that the control program may be stored in another storage device, such as in the ROM 36B. Moreover, in the present exemplary embodiment, the database for tablet management is configured in the storage section 46; however, the database may be configured in another external storage device.

Moreover, the data processing device 36 may be connected to various drives. Various drives refers to devices that read data from, and write data to, a computer readable portable storage medium such as a flexible disk, a magneto-optical disk, or a CD-ROM. When such various drives are provided, the control program may be recorded on a portable storage medium, and read and executed using the appropriate drive.

Data Structure

Explanation follows regarding data structure of the database.

Figures 6A, 6B:
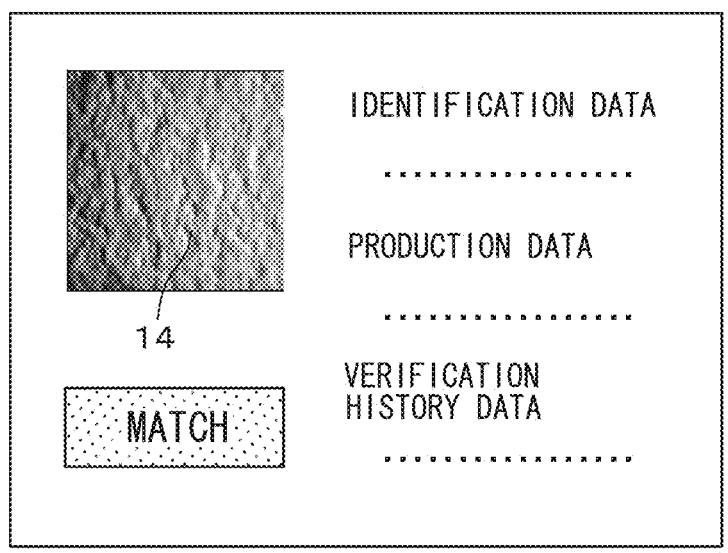
FIG. 6A is a schematic drawing illustrating an example of a database data structure.
FIG. 6B is a schematic drawing illustrating an example of a display screen displaying a registered image.

FIG. 6A is a schematic diagram illustrating an example of data structure of the database. As illustrated in FIG. 6A, the image data of the registered images 14 (registered image data) of the tablets 10 is stored associated with identification data, production data, and verification history data of the respective tablets 10. Identification numbers are one example of identification data of the tablets 10. Data such as lot number (production number), manufacturer, and date of production are examples of production data of the tablet 10. Verification device (the IP address of a terminal device that made the verification request) and verification date are examples of verification history data of the tablet 10.

FIG. 6B is a schematic diagram illustrating an example of a display screen displaying a registered image 14. After the tablet management device 22 has performed verification processing (authenticity determination) in response to a verification instruction from the terminal device 26, the user of the terminal device 26 is notified of the verification results (determination results). In cases in which a registered image 14 matching the verification image 34 has been found and the corresponding tablet 10 has been identified, the terminal device 26 may acquire data associated with the identified tablet 10 as well as the verification results. The data of the identified tablet 10 may be displayed to the user together with the verification results.

For example, as illustrated in FIG. 6B, a display section of the terminal device 26 displays a display screen showing a verification result such as "matched (genuine)" or "not matched (counterfeit)", the registered image 14 of the identified tablet 10, and the identification data, production data, and verification history data of the identified tablet 10.

Terminal Device

Explanation follows regarding electrical configuration of the terminal devices.

The terminal device 24 and the terminal device 26 each have the same configuration as the tablet management device 22 illustrated in FIG. 5, other than in that the tablet management database is absent, and so simplified explanation is given thereof. Similarly to the tablet management device 22, the terminal device 24 and terminal device 26 are respectively configured by data processing devices such as computers and peripheral devices, and each include a data processing device, an imaging section, a display section, an input section, a communications section, and a storage section. The data processing device includes a CPU, ROM, RAM, non-volatile memory and an I/O, and the CPU, ROM, RAM, non-volatile memory, and I/O are respectively connected together through a bus.

Imaging Section

Explanation follows regarding the imaging section that images tablet surface images (see FIG. 4).

An image of the surface of a tablet 10 subject to management (a registered image) is imaged by the imaging section 38 of the tablet management device 22, or by the imaging section of the terminal device 24. The registered image data acquired by imaging is, for example, transmitted from the terminal device 24 to the tablet management device 22, and is stored in the storage section 46 of the tablet management device 22. An image of the surface of a tablet 30 subject to determination (a verification image) is imaged by the imaging section of the terminal device 26. The captured verification image data thus acquired is transmitted from the terminal device 26 to the tablet management device 22, and is verified with the registered images in the database.

As described above, the graphic resolution of the registered images is set in a range of from 400 pixels per inch to 900 pixels per inch. The imaging section that acquires the registered images therefore employs an imaging device such as a camera or an image sensor equipped with a function for imaging surface images of the tablet 10 at the above graphic resolution. The imaging section that acquires the verification images employs an imaging device equipped with a function for imaging surface images of the capture tablet 30 at the same graphic resolution as the registered images. For example, the respective imaging sections may employ imaging devices equipped with a function to capture images at a graphic resolution of 600 pixels per inch (600 dpi) and 256 monochromatic gradations (8-bit grayscale).

Figure 7:
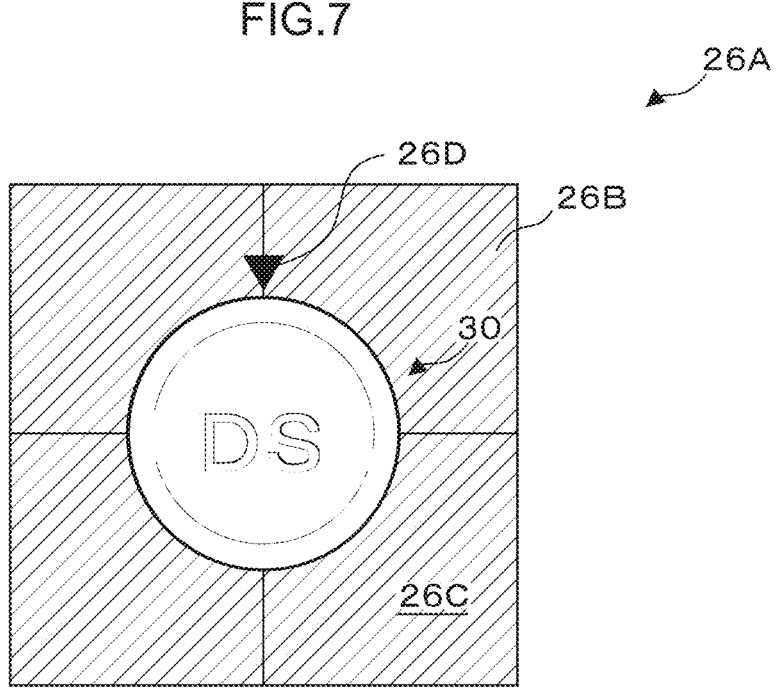
FIG. 7 is a plan view illustrating an example of a positioning means of an imaging section.

Moreover, as illustrated in FIG. 7, the imaging section 26A of the terminal device 26 that images the verification images may include a positioning means to determine the capture position of the tablet 30 that is subject to determination. In this example, a front face 26C of an imaging stage 26B on which the tablet 30 is placed is applied with a positioning marker 26D for identifying a capture position and capture orientation. Note that the positioning means is not limited to the illustrated marker or similar. For example, the positioning means may be configured by a recessed portion, such as a holder or pocket, that is indented in the shape of the tablets subject to management.

When the tablet subject to management has an imprint or the like serving as a marker, the capture position of the tablet 30 may be determined based on the marker of the tablet and the positioning marker 26D of the imaging stage 26B. The scan region of the tablet is disposed with a specific positional relationship to the marker (imprint) of the tablet, such as at a position where the text of the imprint can be properly read. The verification image is imaged in the same orientation as the registered image by disposing the scan region 32 of the tablet 30 in the specific positional relationship with respect to the marker (imprint) of the tablet 30. Matching the orientation of the verification image with the orientation of the registered image eliminates the need to perform rotation correction or the like during verification.

Tablet Management Processing

Explanation follows regarding tablet management processing.

Figure 8:
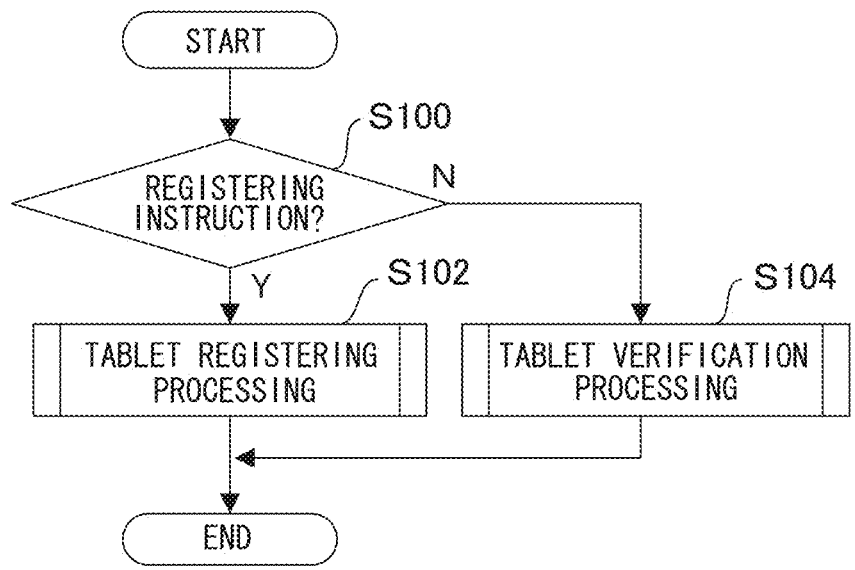
FIG. 8 is a flow chart illustrating a processing routine of "tablet management processing".

FIG. 8 is a flow chart illustrating a processing routine of "tablet management processing". This tablet management processing is executed by the CPU 36A of the tablet management device 22. The tablet management device 22 receives a registering instruction from the terminal device 24 deployed in the production process, and receives a verification instruction from the terminal device 26 deployed in the distribution stage. The "tablet management processing" illustrated in FIG. 8 begins on receipt of a registering instruction or a verification instruction by the tablet management device 22.

First, at step 100, determination is made as to whether or not the received instruction is a registering instruction. If it is a registering instruction, determination is affirmative at step 100 and processing proceeds to step 102. At the next step 102, "tablet registering processing" is executed and the routine ends. If it is a verification instruction, determination is negative at step 100 and processing proceeds to step 104. At the next step 104, "tablet verification processing" is executed and the routine is ended.

Tablet Registering Processing

Explanation follows regarding tablet registering processing.

Figure 9:
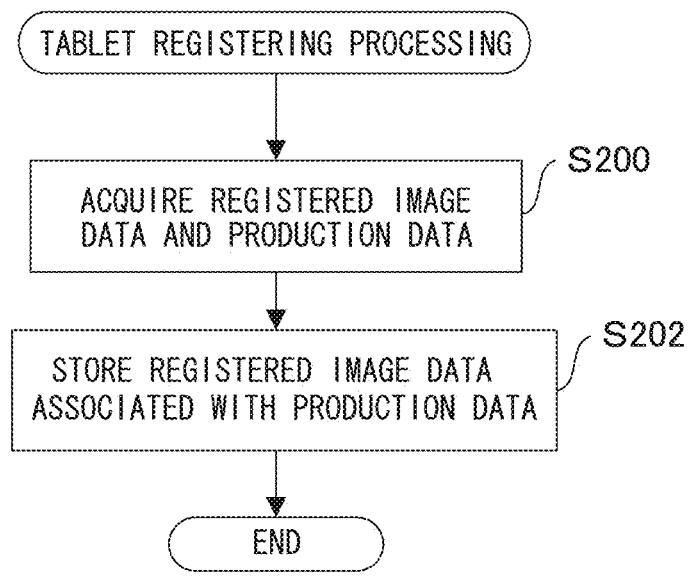
FIG. 9 is a flow chart illustrating a processing routine of "tablet registering processing".

FIG. 9 is a flow chart illustrating a processing routine of "tablet registering processing".

First, at step 200, registered image data corresponding to the registered image of the tablet subject to management, and production data for the tablet corresponding to the registered image, are acquired. For example, transmission of the registered image data, etc., is requested in response to the registering instruction from the terminal device 24, and the registered image data and the production data is acquired from the terminal device 24.

Next, at step 202, the registered image data of the acquired registered image is stored in the storage section 46 associated with the production data of the tablet corresponding to the registered image, as illustrated in FIG. 6A, and the routine is ended. Registered images of plural tablets subject to management are registered in the database in this manner.

Outline Explanation of Tablet Verification Processing

Outline explanation follows regarding tablet verification processing. Note that Japanese Patent No. 4103826 describes a paper fingerprint verification method in detail. In this paper fingerprint verification method, the position of a scan region from which a registered image is scanned is identified using a position marker or the like. Moreover, in the paper fingerprint verification method, the registered image data of the registered images is encoded, and recorded as a code on the paper. The code on the paper is scanned to decode the registered image data.

In cases in which the subject is a tablet, the position of the scan region is not clearly identified. It is moreover difficult to apply a code representing registered image data to an individual tablet. Accordingly, as described above, the orientation of the verification image and the orientation of the registered image are aligned with each other by capturing the verification image at the same orientation as the registered image. Moreover, as described above, the registered image and the verification image are set with graphic resolution in the range of from 400 pixels per inch to 900 pixels per inch, thus stably obtaining the requisite image data for unique tablet identification from tablets with a small diameter φ. With the exception of these points, tablet verification processing is performed in a similar manner to the verification method described in Japanese Patent No. 4103826.

Note that the verification images are imaged at the same graphic resolution and with the same gradations as the registered images. The verification images are moreover imaged over a wider region than the registered images, and in cases in which the tablet subject to determination is a tablet subject to management (genuine), the registered image is contained within the verification image.

Simple explanation follows outlining tablet verification processing.

A region of the verification image overlapping with the registered image is referred to as a "partial image". Correlation values between the partial image and the registered image are computed repeatedly while moving the registered image within the verification image. The correlation values between the partial image and the registered image are computed using the normalized correlation method according to Equation (1) below.

$$F = \{f_i\}_{i=0}^{N-1} \quad G = \{g_i\}_{i=0}^{N-1} \qquad (1)$$

$$\text{Correlation Value} = \frac{\sum_{n=0}^{N-1}(f_n - f_{AVE})(g_n - g_{AVE})}{\sqrt{\sum_{n=0}^{N-1}(f_n - f_{AVE})^2}\sqrt{\sum_{n=0}^{N-1}(g_n - g_{AVE})^2}}$$

F is the registered image, and f, refers to brightness values of the individual pixels of the registered image. N is the total number of pixels in the registered image (or in the partial image). G is the partial image, and g, refers to brightness values of the individual pixels of the partial image. $f_{AVE}$ is the average value of the individual pixels of the registered image, and $g_{AVE}$ is the average value of brightness values of the individual pixels of the partial image.

Plural correlation values are obtained by repeatedly computing the correlation values while moving the registered image in a horizontal direction or a vertical direction, one pixel at a time. Taking the number of pixels in the registered image as m×n, and the number of pixels in the verification image as M×N, (M−m+1)×(N−n+1) correlation values are acquired for a single verification image. Among the plural correlation values acquired, the "maximum value of the correlation values" is taken as a first feature amount.

A "normalized score of the maximum value of the correlation values" is further acquired as a second feature amount. This is referred to below simply as the "normalized score". The "normalized score" is a feature amount expressing the distribution of the correlation values, and is derived using Equation (2) below.

Normalized score=(maximum value of the correlation values−average correlation value)÷standard deviation of correlation values (2)

When there is high correlation between a registered image and a verification image, the maximum value of the correlation values has a high value, and the normalized score also becomes a high value. A "first threshold value" is set as a determination criterion for the maximum value of the correlation values. A "second threshold value" is set as a determination criterion for the normalized score.

Determination may be made based on the maximum value of the correlation values alone. If the maximum value of the correlation values is the first threshold value or greater, the tablet of the verification image is determined to be the tablet of the registered image. Namely, the tablet subject to determination is determined to be a genuine tablet subject to management. Conversely, if the maximum value of the correlation values is lower than the first threshold value, the tablet of the verification image is determined not to be a tablet of the registered images. Namely, the tablet subject to determination is determined to be a counterfeit tablet not subject to management.

Alternatively, determination may be made based on the normalized score alone. If the normalized score is the second threshold value or greater, the tablet of the verification image is determined to be the tablet of the registered image (a genuine tablet that is subject to management). Conversely, if the normalized score is below the second threshold value, the tablet of the verification image is determined not to be a tablet of the registered images (a counterfeit tablet that is not subject to management).

Determination precision improves if determination is made using both the maximum value of the correlation values and the normalized score. In such cases, the tablet of the verification image is determined to be the tablet of the registered image (a genuine tablet that is subject to management) if the maximum value of the correlation values is the first threshold value or greater and the normalized score is the second threshold value or greater. Conversely, the tablet of the verification image is determined not to be a tablet of the registered images (a counterfeit tablet that is not subject to management) if the maximum value of the correlation values is below the first threshold value, or the normalized score is below the second threshold value, or both.

The "first threshold value" of the maximum value of the correlation values and the "second threshold value" of the normalized score are respectively set so as to prevent false determination from occurring. In authenticity determination, false determination includes cases in which genuine is falsely determined to be counterfeit, and cases in which counterfeit is falsely determined to be genuine. The rate of false determination of genuine as counterfeit is referred to as the "False Rejection Rate (FRR)", and the rate of false determination of counterfeit as genuine is referred to as the "False Acceptance Rate (FAR)". The "first threshold value" and the "second threshold value" are respectively set so as to give both an "FRR" and an "FAR" of 0%.

Specifically, authenticity determination testing is performed on plural tablets that are a mixture of genuine and counterfeit, and a distribution (histogram) is derived of maximum values of the obtained correlation values. If there is a range in which the maximum values of the correlation values give both an "FRR" and an "FAR" of 0%, then the "first threshold value" is set within this range. In other words, the wider the range within which both the "FRR" and the "FAR" are 0%, the greater the difference between the distribution ranges of genuine and counterfeit, meaning that authenticity determination becomes easier. Similarly, for the normalized scores the distribution of the normalized scores is derived, and the "second threshold value" is set within a range giving both an "FRR" and an "FAR" of 0%.

Tablet Verification Processing Routine

Explanation follows regarding a specific tablet verification processing routine.

Figure 10A:
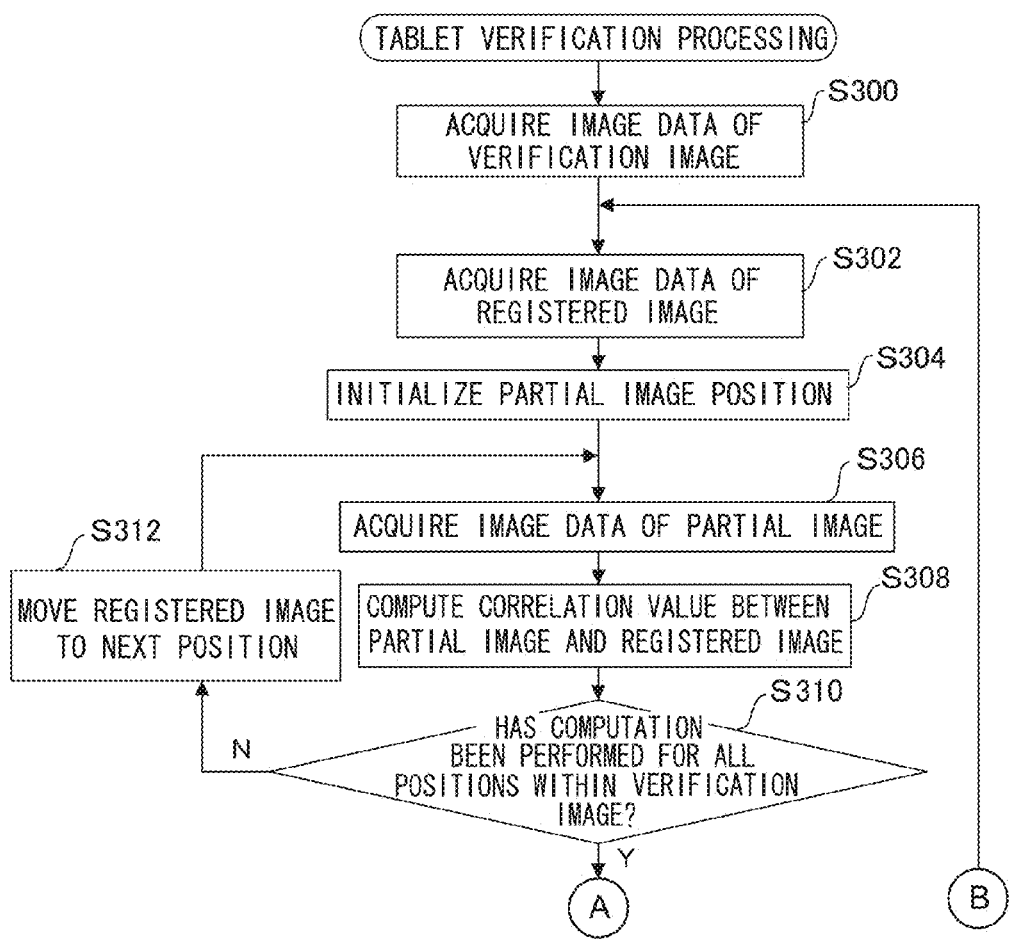

FIGS. 10A and 10B illustrate a flow chart illustrating a processing routine of "tablet verification processing".

First, at step 300, verification image data of a verification image of the tablet subject to determination is acquired. For example, transmission of verification image data and the like is requested in response to a verification instruction from the terminal device 26, and the verification image data are obtained from the terminal device 26.

As described above, plural registered images are registered in the database of the tablet management device 22, and verification is performed with each of the plural registered images. Accordingly, at the next step 302, one of the registered images in the database is selected, and image data (image data expressing brightness values of each pixel) of the selected registered image is acquired.

Moreover, as described above, correlation values between the partial image and the registered image are computed repeatedly while moving the registered image within the verification image. Accordingly, at the next step 304, the position of the partial image within the verification image is initialized. Next, at step 306, image data (image data expressing brightness values of each pixel) of the partial image is acquired. Next, at step 308, a correlation value between the partial image and the registered image is computed using a normalized correlation method, using Equation (1) described above. The computed correlation value thus obtained is stored in the RAM 36C or the like.

Next, at step 310, determination is made as to whether or not correlation values have been acquired for all positions within the verification image. If the determination at step 310 is negative, processing proceeds to step 312, where the registered image is moved to the next position, and then processing returns to step 306. The routine of step 306 to step 312 is repeated until correlation values have been acquired for all positions within the verification image.

When computation of the correlation values has been completed, determination is affirmative at step 310, and processing proceeds to step 314, where the maximum value of the correlation values is acquired from the plural correlation values acquired by computation. At the next step 316, the standard deviation and average value of the plural correlation values are derived, and a normalized score of the maximum value of the correlation values is obtained by performing computation using Equation (2), by using the obtained standard deviation and average value, and the maximum value of the correlation values derived at step 314.

Next, at step 318, determination is made as to whether or not the maximum value of the correlation values acquired at step 314 is the first threshold value or greater, and whether or not the normalized score acquired at step 316 is the second threshold value or greater. If determination is affirmative at step 318, processing proceeds to step 320, and a determination result is output that the tablet subject to determination is "a genuine tablet that is subject to management".

For example, the user is notified of the determination result by, for example, displaying the determination result on the display section or the like of the terminal device 26 that made the verification instruction. The registered image and/or the production data of the tablet corresponding to the registered image may be displayed as well as the determination result. Next, at step 322, the verification history data is registered in the database of the tablet management device 22, and the tablet verification processing routine is ended.

If determination is negative at step 318, processing transitions to step 324, and determination is made as to whether or not verification has been performed for all of the registered images. If determination is negative at step 324, processing proceeds to step 326, the next registered image is selected, and processing returns to step 302. The routine from step 302 to step 324 is repeated until verification has been made with all of the registered images, unless a determination result is obtained partway through the determination that indicates that the tablet is "a genuine tablet that is subject to management".

If determination is affirmative at step 324, processing proceeds to step 328, a determination result that the tablet subject to determination is "a counterfeit tablet that is not subject to management" is output, and the tablet verification processing routine is ended. The authenticity of the tablet subject to determination is determined using the simple processing as described above. The tablet subject to determination is moreover uniquely identified.

MODIFIED EXAMPLE

Configurations of the tablets, the method of producing tablets, the tablet management device, the tablet verification device and the program described in the above exemplary embodiment are merely examples thereof, and these configurations may obviously be modified within a range that does not depart from the spirit of the present invention. For example, the sequence of each of the steps illustrated in the flow charts may be changed.

EXAMPLES

Examples are used to provide more specific explanation regarding the present invention, however the scope of the present invention is not limited to these Examples.

Example 1

Tablets according to Example 1 were manufactured using the following protocol, and tablet surface analysis was performed on the obtained tablets.

Tablet Production Protocol (1) Uncoated Tablet Manufacture

Binder was added to a mixture of main components, excipients, and disintegrant, granulation was performed, and granules were obtained. Lubricant, excipient and disintegrant were added to, and mixed together with the obtained granules, and granules to be tableted were obtained. The obtained granules to be tableted were compression molded and uncoated tablets were produced with a weight of approximately 250 mg, a circular shape in plan view, and a diameter φ of 8 mm.

(2) Coating Liquid Preparation

A coating liquid for use in a film coating was obtained as a suspension of a coating component, composed as illustrated in Table 1 below, dispersed in water at 12 w/v %. The amount of coating component was set such that the proportion of the weight of the coating component to the weight of an uncoated tablet was approximately 3.6% by weight. Note that the following products were used for the respective components listed in Table 1: titanium oxide (trade name: A-HR, manufactured by Freund Corporation), hypromellose (trade name: TC-5R, manufactured by Shin-Etsu Chemical Co., Ltd.), polyethylene glycol (trade name: Macrogol 6000, manufactured by NOF Corporation).

TABLE 1

| Coating component | Formula (mg/tablet) |
| --- | --- |
| Titanium Oxide | 1.80 |
| Hypromellose | 6.30 |
| Polyethylene glycol | 0.90 |
| Coating component total | 9.00 |

(3) Coated Tablet Manufacture 10 kg of the uncoated tablets obtained by (1) above were loaded into a pan coating machine (Driacoater 650, manufactured by Powrex Corporation) with a pan capacity of 15 liters (L). The uncoated tablets were spray coated with the coating liquid obtained by (2) above under the following Conditions A, obtaining coated tablets that were covered by approximately 9 mg of the coating component per tablet after drying. In the obtained coated tablets, the proportion of the weight of the coating component to the weight of the uncoated tablet was approximately 3.6% by weight.

Conditions A

The uncoated tablets were heated for approximately 5 minutes at an air supply temperature of 65° C., until the temperature of the exhausted air reached 45° C. Next, the uncoated tablets were spray coated with the coating liquid for approximately 330 minutes, with an initial air supply temperature of 60° C., an air supply rate of 6.5 m³/min, a sprayed liquid speed of 15 mL/min, a sprayed air amount of 100 NL/min (NL: normal liters), and pan revolution speed from 5 to 8 rpm (gradually increasing from 5 rpm to 8 rpm), while maintaining the humidity of exhausted air at 14% RH. After completion of spray coating, drying was performed until the temperature of the exhausted air reached 55° C. After completion of drying, cooling was performed until the temperature of the exhausted air reached 40° C., and the obtained tablets were then removed from the pan coating machine.

Figure 11:
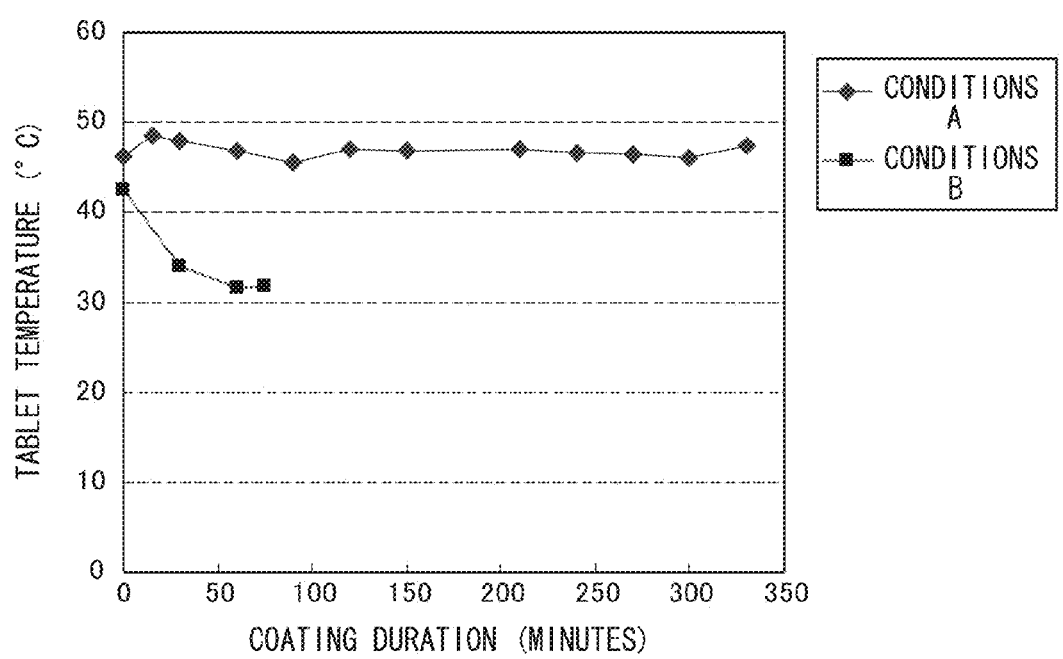
FIG. 11 is a graph illustrating change in tablet temperature over time during spray coating.
Figure 12:
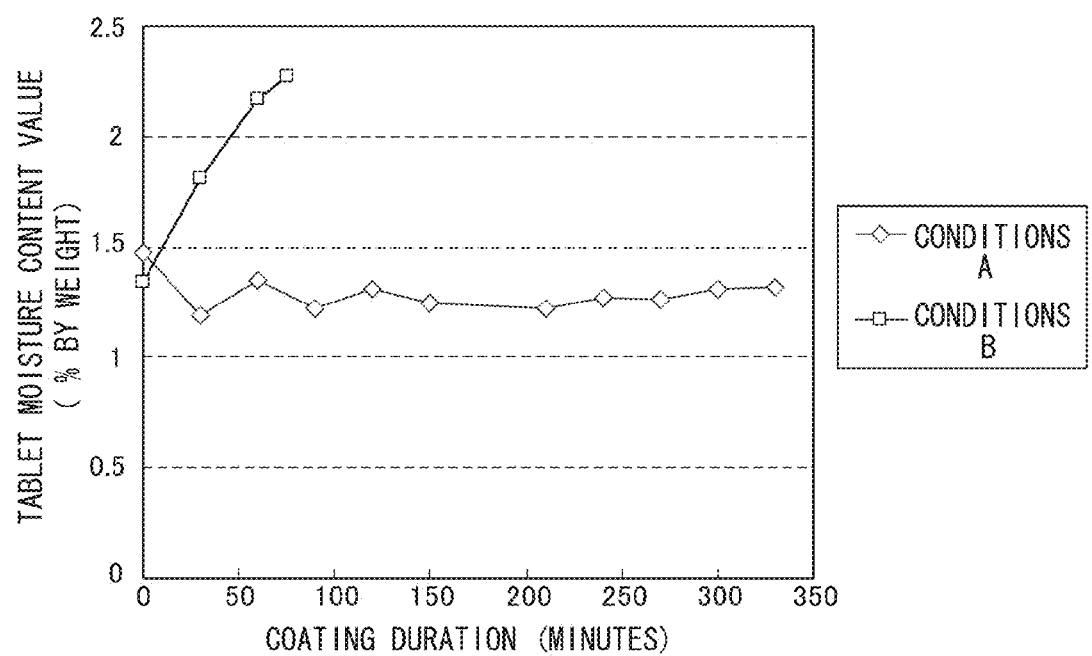
FIG. 12 is a graph illustrating change in tablet moisture content values over time during spray coating.

FIG. 11 illustrates change over time in the temperature of the tablets during spray coating. The horizontal axis represents the coating duration. The unit used is "minutes". The vertical axis represents the tablet temperature. The unit used is "° C.". Note that "coating duration" refers to the time elapsed since the start of spray coating. FIG. 12 illustrates change over time in the tablet moisture content value during spray coating. The horizontal axis represents the coating duration (unit: minutes). The vertical axis represents the tablet moisture content value. The unit used is "% by weight". Contactless measurement of the tablet temperature is made using a radiation thermometer. The tablet moisture content value is measured for tablet sampling, at a heating temperature of 80° C. using a moisture meter adopting heating-loss method.

As can be seen from FIG. 11 and FIG. 12, under Conditions A, the tablet temperature at the time of completion of spray coating is 47° C., and the tablet moisture content value at the time of completion of spray coating is 1.3% by weight.

Tablet Surface Analysis 150 tablets according to Example 1 (produced under Conditions A) were prepared. The surface of each of the 150 tablets was scanned at a graphic resolution of 600 dpi in 8-bit grayscale gradations, using an image sensor. Image data of a 32 pixel×32 pixel region at a central portion of each tablet was registered in advance as "registered image" data. For convenience, the tablets registered in advance as "registered image" data are referred to below as "genuine".

A further 750 unregistered tablets, produced under the same Conditions A, were prepared separately to the 150 registered tablets. For convenience, these 750 tablets are referred to below as "counterfeit". Namely, the difference between "genuine" and "counterfeit" lay in whether or not they were registered, where being registered means being subject to management. The 150 genuine tablets and the 750 counterfeit tablets were added together to give a total of 900 tablets for testing. The surface of each of the 900 tablets for testing was scanned at a graphic resolution of 600 dpi in 8-bit grayscale gradations using an image sensor, and image data of a 64 pixel×64 pixel region at a central portion of each tablet was acquired as "verification image" data.

Figure 13:
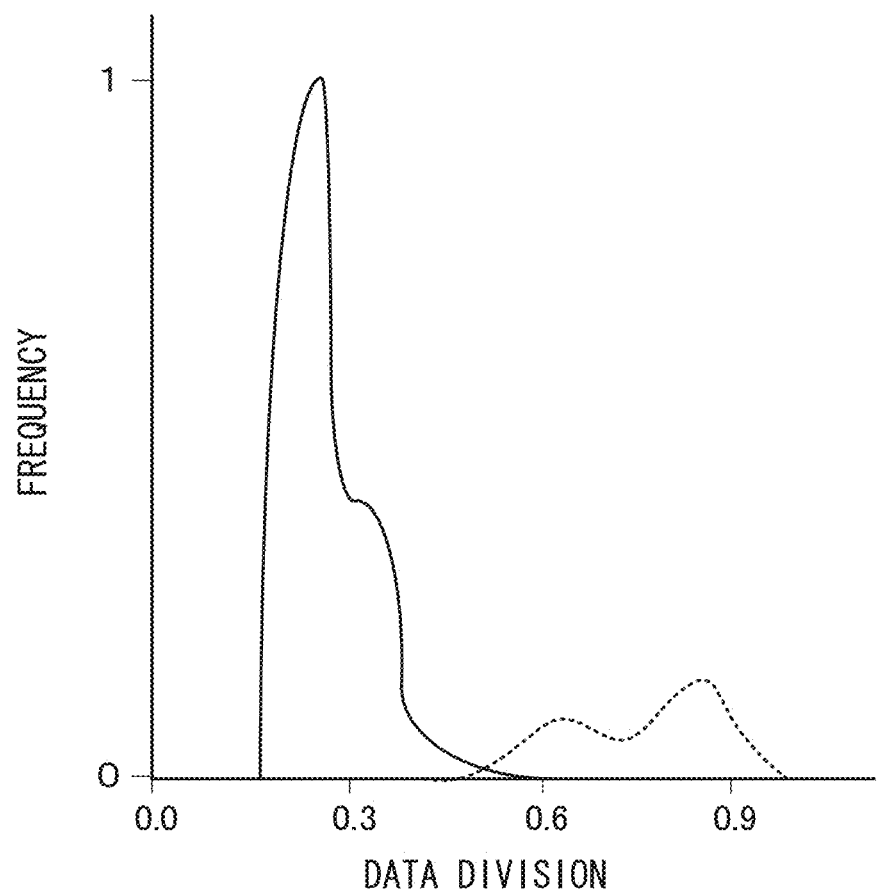
FIG. 13 is a graph illustrating computation results (distribution of maximum values of correlation values) of Example 1.
Figure 14:
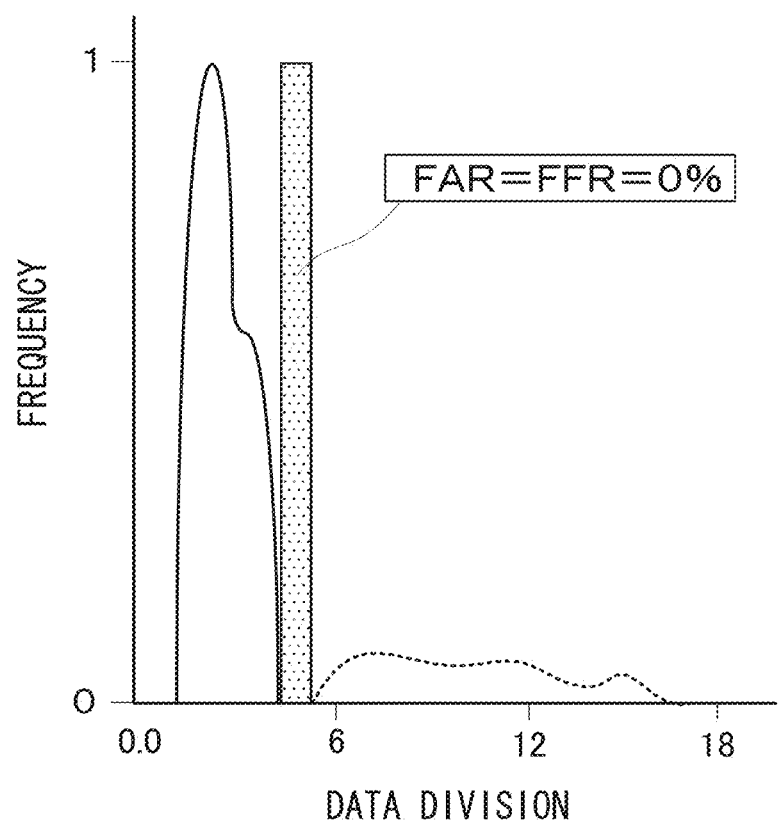
FIG. 14 is a graph illustrating computation results (distribution of normalized scores) of Example 1.

For the 900 "verification images", tablet verification processing was performed against each of the 150 "registered images" using the method described above. Plural "maximum values of correlation values" and plural "normalized scores" were obtained using the computation methods described above. FIG. 13 illustrates computation results for Example 1 (distribution of the maximum values of the correlation values). FIG. 14 illustrates computation results for Example 1 (distribution of the normalized scores).

In FIG. 13 and FIG. 14, the horizontal axis represents data divisions, and the vertical axis represents normalized frequency. The solid line represents the distribution of counterfeit, and the broken line represents the distribution of genuine.

As can be seen from FIG. 13, examination of the distribution of the maximum values of the correlation values reveals that there is an overlap between the distribution of counterfeit and the distribution of genuine, and there is no range in which both the FRR and the FAR are 0%. Accordingly, a determination threshold value cannot be set using the maximum values of the correlation values. However, as can be seen from FIG. 14, examination of the distribution of the normalized scores reveals that a range is present in which the FRR and the FAR are both 0% (the shaded area). A determination threshold value can accordingly be set using the normalized scores. However, the settable range of the determination threshold value is very narrow.

In this case, a tablet is determined to be genuine if the normalized score is a threshold value or greater, and a tablet is determined to be counterfeit if the normalized score is below the threshold value. However, the only feature amount serving as a determination condition is the normalized score, and the settable range of the determination threshold value is very narrow, even for the normalized scores. Tablets produced under Conditions A are therefore considered to be borderline for determinability.

Example 2

Tablets according to Example 2 were produced using the following protocol, and tablet surface analysis was performed on the obtained tablets.

Tablet Production Protocol

The tablets according to Example 2 were produced using a similar protocol to those of Example 1, with the exception that the coating conditions in the coated tablet production conditions of Protocol (3) were changed from "Conditions A" to "Conditions B". The coated tablets obtained were coated by approximately 9 mg of the coating component per tablet after drying.

Conditions B

The uncoated tablets were pre-heated for approximately 5 minutes at an air supply temperature of 65° C. until the temperature of the exhausted air reached 45° C. Next, the uncoated tablets were spray coated with the coating liquid for approximately 70 minutes, with an initial air supply temperature of 60° C., an air supply rate of 5.0 m³/min, a sprayed liquid speed of 40 mL/min, a sprayed air amount of 100 NL/min (NL: normal liters), and pan revolution speed from 5 to 8 rpm (gradually increasing from 5 rpm to 8 rpm), while maintaining the humidity of the exhausted air at 30% RH. After completion of spray coating, drying was performed until the temperature of the exhausted air reached 55° C. After completion of drying, cooling was performed until the temperature of exhausted air reached 40° C., and the obtained tablets were then removed from the pan coating machine.

As can be seen from FIG. 11 and FIG. 12, under Conditions B, the tablet temperature at the time of completion of spray coating was 32° C., and the tablet moisture content value at the time of completion of spray coating was 2.3% by weight.

Tablet Surface Analysis

Figure 15:
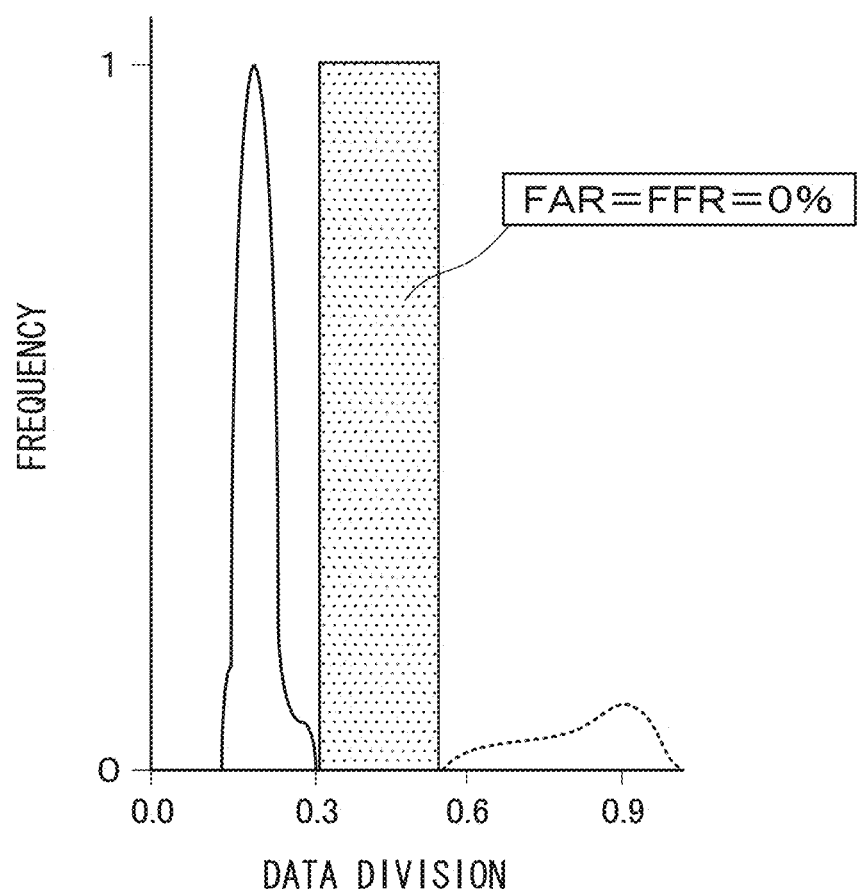
FIG. 15 is a graph illustrating computation results (distribution of maximum values of correlation values) of Example 2.
Figure 16:
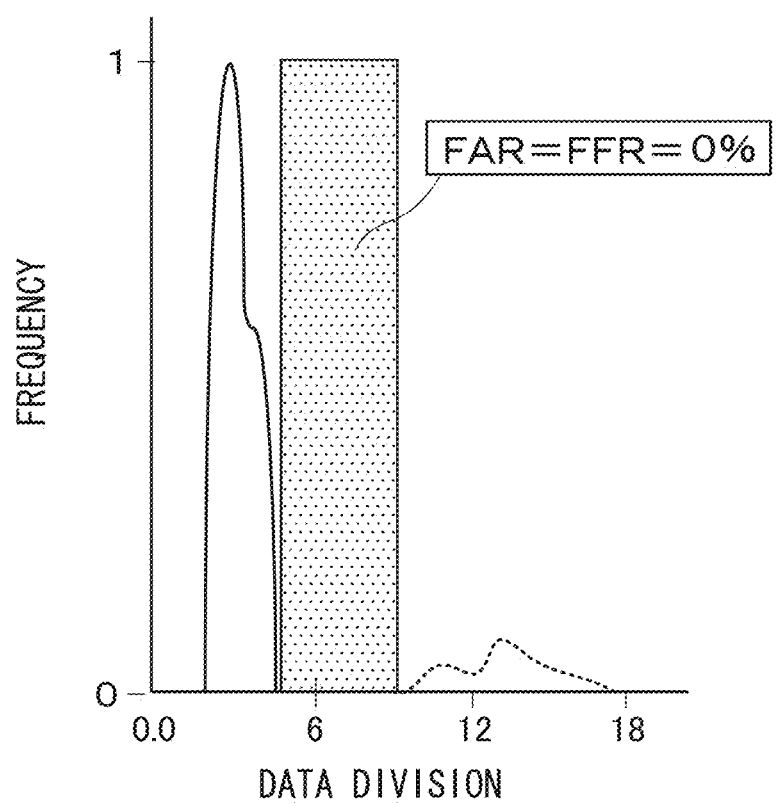
FIG. 16 is a graph illustrating computation results (distribution of normalized scores) of Example 2.

Analysis was performed using a similar method to that of Example 1. 150 tablets according to Example 2 (produced under Conditions B) were prepared, and similarly, image data obtained by scanning these 150 tablets (referred to as "genuine" for convenience) was registered in advance as "registered image" data. A further 750 unregistered tablets were produced under the same Conditions B, separately to the 150 registered tablets (referred to as "counterfeit" for convenience). Once again, the difference between "genuine" and "counterfeit" lay in whether or not they were registered, and whether or not they were subject to management. Similarly to in Example 1, the total of 900 tablets were subjected to tablet verification processing, and plural "maximum values of the correlation values" and plural "normalized scores" were obtained. FIG. 15 illustrates computation results for Example 2 (distribution of the maximum values of the correlation values). FIG. 16 illustrates computation results for Example 2 (distribution of the normalized scores).

In FIG. 15 and FIG. 16, the horizontal axis represents data divisions, and the vertical axis represents normalized frequency. The solid line represents the distribution of counterfeit, and the broken line represents the distribution of genuine.

As can be seen from FIG. 15, examination of the distribution of the maximum value of the correlation values reveals that there is a range present where both the FRR and the FAR are 0% (the shaded area), enabling a determination threshold value to be set using the maximum values of the correlation values. As can be seen from FIG. 16, examination of the distribution of the normalized scores reveals that there is a range present where both the FRR and the FAR are 0% (the shaded area), enabling a determination threshold value to be set using the normalized scores. In each case, it can be seen that the settable region of the determination threshold value is wider than in Example 1.

In this case, either one of the maximum value of the correlation values or the normalized scores may be set as a determination condition. A tablet is determined to be genuine if either the maximum value of the correlation values or the normalized score is a threshold value or greater, and a tablet is determined to be counterfeit if either is below the threshold value.

From the tablet surface analysis results of Example 1 and Example 2, it is conjectured that the undulating shapes of the tablet surfaces in each of the Examples are formed according to the drying efficiency during spray coating in the coating process. In Example 1, the feature amount as the determination condition is limited to the normalized score, and even using the normalized score, the settable range of the determination threshold value is very narrow. The Conditions A in Example 1 (humidity of the exhausted air of 14% RH during spray coating) is accordingly understood as being a borderline condition for application of the verification determination method of the tablet management processing according to the present exemplary embodiment. Namely, when the humidity of exhausted air during spray coating is set at 14% RH or higher, it is possible to produce tablets enabling unique identification based on image data.

The disclosure of Japanese Patent Application No. 2012-062605 is incorporated in its entirety in the present specification by reference. Moreover, all publications, patent applications and technical standards mentioned in the present specification are incorporated by reference in the present specification to the same extent as if each individual publication, patent application, or technical standard was specifically and individually indicated to be incorporated by reference.

The invention claimed is:

1. A method of producing a tablet in which an uncoated tablet is coated by a coating agent, the method comprising:
a coating process of coating uncoated tablets with a coating agent and forming outer surfaces of tablets by spray coating the coating agent onto tablets that are churned and tumbled inside a container, and drying the tablets inside the container by supplying drying air into the container and exhausting air from the container,
wherein spray coating conditions, including air supply temperature, air supply rate, and spray speed, are controlled according to a weight of the coating agent with which the uncoated tablets are coated, such that a humidity of air exhausted during spray coating is within a range of from 14% RH to 30% RH and such that an air supply temperature is at 60° C.

2. The method of producing the tablet of claim 1, wherein the humidity is within a range of from greater than 20% RH to less than 25% RH.

3. The method of producing a tablet of claim 1, wherein the spray coating conditions are controlled such that a temperature of the tablets during spray coating is 47° C. or lower.

4. The method of producing the tablet of claim 1, wherein the spray coating conditions are further controlled such that an air supply rate is between 5.0 m³/min and 6.5 m³/min.

5. The method of producing the tablet of claim 1, wherein the spray coating conditions are further controlled such that a sprayed liquid speed is between 15 mL/min and 40 mL/min.

6. The method of producing the tablet of claim 1, wherein the spray coating conditions are further controlled such that a sprayed air amount is at 100 NL (normal liters)/min.

7. The method of producing the tablet of claim 1, wherein the spray coating conditions are further controlled such that a pan revolution speed is gradually increased from 5 rpm to 8 rpm during the spray coating.

8. The method of producing a tablet of claim 1, wherein the spray coating conditions are controlled such that in cases in which a proportion of a weight of the coating agent to a weight of the uncoated tablets is 3.6% by weight, a moisture content of the tablets on completion of spray coating is between 1.3% by weight and 2.3% by weight.

9. The method of producing the tablet of claim 8, wherein the moisture content is measured at 80° C.

10. The method of producing a tablet of claim 1, wherein, after completion of the coating process:
a plurality of the tablets are arrayed such that the plurality of tablets form a line in a predetermined direction; and
a marker that identifies an orientation of a predetermined scan region is applied to a surface of each of the arrayed plurality of tablets, and a plurality of image data is acquired by scanning the predetermined scan region on the surface of each of the arrayed plurality of tablets.

* * * * *